US012776402B2

(12) United States Patent
Loebig et al.

(10) Patent No.: US 12,776,402 B2
(45) **Date of Patent: *Oct. 27, 2026**

(54) SYSTEM AND METHOD FOR DISPENSING MEDICATION

(71) Applicant: CareFusion 303, Inc., San Diego, CA (US)

(72) Inventors: Scott Loebig, San Diego, CA (US); Cynthia Yamaga, San Diego, CA (US); Abhikesh Nag, San Diego, CA (US)

(73) Assignee: CareFusion 303, Inc., San Diego, CA (US)

( * ) Notice: Subject to any disclaimer, the term of this patent is extended or adjusted under 35 U.S.C. 154(b) by 194 days.

This patent is subject to a terminal disclaimer.

(21) Appl. No.: 17/363,713

(22) Filed: Jun. 30, 2021

(65) Prior Publication Data

US 2021/0343386 A1 Nov. 4, 2021

Related U.S. Application Data

(63) Continuation of application No. 15/887,222, filed on Feb. 2, 2018, now Pat. No. 11,081,220.

(51) Int. Cl.
*G16H 20/13* (2018.01)
*G06N 20/00* (2019.01)

(52) U.S. Cl.
CPC ............ *G16H 20/13* (2018.01); *G06N 20/00* (2019.01)

(58) Field of Classification Search
CPC ........ G16H 20/13; G16H 40/67; G16H 40/63; G07F 17/0092; G07F 5/18;
(Continued)

(56) References Cited

U.S. PATENT DOCUMENTS 4,551,133 A 11/1985 Zegers de Beyl et al.
4,693,804 A 9/1987 Serwer
(Continued)

FOREIGN PATENT DOCUMENTS

AU 2017 279 693 A1 1/2018
AU 2018335288 B2 * 8/2023 ............ G06F 21/32
(Continued)

OTHER PUBLICATIONS

Benjamin, X.C. et al. (2012). "Visual identification of medicine boxes using features matching." *IEEE International Conference on Virtual Environments Human-Computer Interfaces and Measurement Systems* (*VECIMS*) *Proceedings*, 43-47. Doi: 10.1109/VECIMS.2012.6273190.
(Continued)

*Primary Examiner* — Dilek B Cobanoglu
(74) *Attorney, Agent, or Firm* — Mintz Levin Cohn Ferris Glovsky and Popeo, P.C.

(57) ABSTRACT

A method for detecting diversion may include receiving, from a dispensing cabinet including medication, data associated with a plurality of individuals accessing the dispensing cabinet to retrieve and/or return the medication. Diversion of the medication may be detected by at least applying, to at least a portion of the data received from the dispensing cabinet, a machine learning model trained to detect diversion. An identity of a first individual responsible for the diversion may be determined based on the data received from the dispensing cabinet. In response to the determination of the first individual as being responsible for the diversion, an investigative workflow may be triggered at the dispensing cabinet. Related systems and articles of manufacture, including apparatuses and computer program products, are also disclosed.

20 Claims, 5 Drawing Sheets

(58) Field of Classification Search
CPC .. G06F 16/9535; A61J 7/0445; G06Q 10/087; G06Q 10/10; G07C 9/00912
USPC .......................................... 700/236; 705/2, 3
See application file for complete search history.

(56) References Cited

U.S. PATENT DOCUMENTS 5,945,651 A 8/1999 Chorosinski et al.
5,961,036 A * 10/1999 Michael .............. G07F 17/0092 221/9
5,991,731 A 11/1999 Colon et al.
6,113,578 A 9/2000 Brown
6,636,780 B1 * 10/2003 Haitin .................. A61G 12/001 700/242
6,650,964 B2 11/2003 Spano, Jr. et al.
6,671,579 B2 12/2003 Spano, Jr. et al.
6,842,736 B1 * 1/2005 Brzozowski ........... G06Q 10/10 705/2
6,868,344 B1 3/2005 Nelson
7,119,689 B2 10/2006 Mallett et al.
7,184,897 B2 2/2007 Nelson
7,275,645 B2 10/2007 Mallett et al.
7,303,081 B2 12/2007 Mallett et al.
7,311,207 B2 12/2007 Mallett et al.
7,318,529 B2 1/2008 Mallett et al.
7,562,025 B2 7/2009 Mallett et al.
7,693,603 B2 * 4/2010 Higham ............. G07C 9/00912 700/242
8,147,479 B1 4/2012 Wach et al.
8,195,328 B2 6/2012 Mallett et al.
8,280,550 B2 10/2012 Levy et al.
8,319,669 B2 11/2012 Weller
8,357,114 B2 1/2013 Poutiatine et al.
8,595,021 B2 11/2013 Mallett et al.
8,606,596 B1 12/2013 Bochenko et al.
8,725,532 B1 5/2014 Ringold
8,738,177 B2 5/2014 van Ooyen et al.
8,768,724 B2 7/2014 Whiddon et al.
8,905,964 B2 12/2014 Poutiatine et al.
9,056,165 B2 6/2015 Steil et al.
9,158,892 B2 10/2015 Levy et al.
9,202,052 B1 12/2015 Fang et al.
9,227,025 B2 1/2016 Butterfield et al.
9,354,178 B2 5/2016 Lee
9,427,520 B2 8/2016 Batch et al.
9,443,370 B2 * 9/2016 Carson ................ G07F 17/0092
9,456,958 B2 10/2016 Reddy et al.
9,523,635 B2 12/2016 Tilden
9,636,273 B1 5/2017 Harris
9,752,935 B2 9/2017 Marquardt et al.
9,796,526 B2 10/2017 Smith et al.
9,817,850 B2 11/2017 Dubbels et al.
9,836,485 B2 12/2017 Dubbels et al.
9,842,196 B2 12/2017 Utech et al.
9,881,129 B1 1/2018 Cave
9,958,324 B1 5/2018 Marquardt et al.
10,032,344 B2 7/2018 Nelson et al.
10,101,269 B2 10/2018 Judge et al.
10,187,288 B2 1/2019 Parker et al.
10,209,176 B2 2/2019 Proskurowski et al.
10,241,038 B2 3/2019 Nishimura et al.
10,249,153 B2 4/2019 Nelson et al.
10,309,832 B2 6/2019 Marquardt et al.
10,345,242 B2 7/2019 Zhao et al.
10,444,060 B2 10/2019 Parker et al.
10,515,722 B2 12/2019 Vahlberg
10,569,015 B2 2/2020 Estes
10,580,525 B2 * 3/2020 Adams ...................... G07F 5/18
10,832,207 B2 11/2020 Vahlberg et al.
10,915,604 B2 * 2/2021 Tribble ............... G06F 16/9535
11,116,892 B2 9/2021 Brady et al.
11,147,914 B2 10/2021 Estes
11,355,237 B2 * 6/2022 Vanderveen ........... G16H 40/67
2003/0158751 A1 8/2003 Suresh et al.
2003/0167190 A1 9/2003 Rincavage et al.
2005/0277873 A1 12/2005 Stewart et al.
2006/0047538 A1 3/2006 Condurso et al.
2006/0064053 A1 3/2006 Bollish et al.
2007/0260487 A1 11/2007 Bartfeld et al.
2008/0059226 A1 3/2008 Melker et al.
2008/0082360 A1 4/2008 Bailey et al.
2008/0140715 A1 6/2008 Hakos
2008/0243055 A1 10/2008 Fathallah et al.
2008/0288430 A1 11/2008 Friedlander et al.
2008/0306796 A1 12/2008 Zimmerman et al.
2008/0319795 A1 12/2008 Poteet et al.
2009/0083231 A1 3/2009 Eberholst et al.
2009/0159608 A1 * 6/2009 Shoenfeld .............. G16H 20/13 700/231
2009/0160646 A1 6/2009 Mackenzie et al.
2009/0187274 A1 * 7/2009 Higham ............. G07C 9/00912 340/657
2010/0042437 A1 * 2/2010 Levy ...................... G16H 40/67 700/242
2010/0169063 A1 7/2010 Yudkovitch et al.
2010/0213250 A1 8/2010 Mallett et al.
2010/0271218 A1 10/2010 Hoag et al.
2011/0016110 A1 1/2011 Egi et al.
2011/0082440 A1 4/2011 Kimmo et al.
2011/0161108 A1 6/2011 Miller et al.
2011/0196304 A1 8/2011 Kramer et al.
2012/0173440 A1 7/2012 Dehlinger et al.
2012/0226447 A1 9/2012 Nelson et al.
2012/0265336 A1 10/2012 Mallett et al.
2012/0305132 A1 12/2012 Maness
2012/0325330 A1 12/2012 Prince et al.
2013/0002429 A1 1/2013 Johnson
2013/0018356 A1 1/2013 Prince et al.
2013/0070090 A1 * 3/2013 Bufalini ................. G16H 20/13 348/143
2013/0144254 A1 6/2013 Amirouche et al.
2013/0253291 A1 9/2013 Dixon et al.
2013/0253700 A1 * 9/2013 Carson ................... G16H 20/13 700/236
2013/0262138 A1 10/2013 Jaskela et al.
2013/0282392 A1 * 10/2013 Wurm .................. G06Q 10/087 705/2
2013/0325727 A1 12/2013 MacDonell et al.
2014/0074284 A1 3/2014 Czaplewski et al.
2014/0081652 A1 3/2014 Klindworth
2014/0149131 A1 5/2014 Bear et al.
2014/0228755 A1 8/2014 Darrah et al.
2014/0249776 A1 9/2014 King et al.
2014/0257832 A1 9/2014 Hermiz et al.
2014/0277707 A1 9/2014 Akdogan et al.
2014/0375324 A1 12/2014 Matsiev et al.
2015/0038898 A1 2/2015 Palmer et al.
2015/0061832 A1 3/2015 Pavlovic et al.
2015/0081324 A1 3/2015 Adjaoute
2015/0109437 A1 4/2015 Yang et al.
2015/0161558 A1 6/2015 Gitchell et al.
2015/0221086 A1 8/2015 Bertram
2015/0272825 A1 10/2015 Lim et al.
2015/0286783 A1 10/2015 Kumar et al.
2015/0294079 A1 10/2015 Bergougnan
2015/0323369 A1 11/2015 Marquardt
2015/0339456 A1 11/2015 Sprintz
2015/0362350 A1 12/2015 Miller et al.
2016/0034274 A1 2/2016 Diao et al.
2016/0062371 A1 3/2016 Davidian et al.
2016/0117478 A1 4/2016 Hanina et al.
2016/0136054 A1 * 5/2016 Bunker ................. A61J 7/0084 340/573.1
2016/0161705 A1 6/2016 Marquardt et al.
2016/0166766 A1 6/2016 Schuster et al.
2016/0259904 A1 * 9/2016 Wilson ................... G16H 40/63
2016/0259911 A1 9/2016 Koester
2016/0283691 A1 9/2016 Ali
2016/0346469 A1 12/2016 Shubinsky et al.
2017/0017760 A1 1/2017 Freese et al.
2017/0032102 A1 2/2017 Skoda
2017/0076065 A1 3/2017 Darr et al.
2017/0083681 A1 3/2017 Sprintz et al.
2017/0103203 A1 4/2017 Sharma et al.

(56) References Cited

U.S. PATENT DOCUMENTS

| | | | |
|---|---|---|---|
| 2017/0108480 | A1 | 4/2017 | Clark et al. |
| 2017/0109480 | A1 * | 4/2017 | Vahlberg ................. G07F 9/002 |
| 2017/0109497 | A1 * | 4/2017 | Tribble ............. G06F 16/24578 |
| 2017/0120035 | A1 | 5/2017 | Butterfield et al. |
| 2017/0199983 | A1 | 7/2017 | Cano et al. |
| 2018/0028408 | A1 * | 2/2018 | Li ......................... A61J 7/0445 |
| 2018/0039736 | A1 | 2/2018 | Williams |
| 2018/0046651 | A1 | 2/2018 | Dubbels et al. |
| 2018/0157803 | A1 | 6/2018 | Mirov |
| 2018/0165417 | A1 | 6/2018 | Hall et al. |
| 2018/0192942 | A1 | 7/2018 | Clark et al. |
| 2018/0203978 | A1 | 7/2018 | Basu et al. |
| 2018/0231415 | A1 | 8/2018 | Marquardt et al. |
| 2018/0247703 | A1 | 8/2018 | D'Amato |
| 2018/0259446 | A1 | 9/2018 | Coffey et al. |
| 2018/0299375 | A1 | 10/2018 | Young et al. |
| 2018/0330824 | A1 | 11/2018 | Athey et al. |
| 2018/0365385 | A1 | 12/2018 | Cooney et al. |
| 2018/0365386 | A1 | 12/2018 | Vanderveen |
| 2019/0088354 | A1 | 3/2019 | Yanowitz et al. |
| 2019/0117883 | A1 | 4/2019 | Abrams et al. |
| 2019/0124118 | A1 | 4/2019 | Swafford |
| 2019/0139638 | A1 | 5/2019 | Keefe et al. |
| 2019/0180862 | A1 | 6/2019 | Wisser et al. |
| 2019/0206540 | A1 | 7/2019 | Agassi et al. |
| 2019/0244699 | A1 | 8/2019 | Loebig et al. |
| 2019/0247703 | A1 | 8/2019 | Welde et al. |
| 2019/0341142 | A1 | 11/2019 | Nag et al. |
| 2020/0098474 | A1 | 3/2020 | Vanderveen |
| 2020/0219611 | A1 | 7/2020 | Nag et al. |
| 2020/0222627 | A1 | 7/2020 | Guerra et al. |
| 2020/0230316 | A1 | 7/2020 | Guerra et al. |
| 2021/0133201 | A1 | 5/2021 | Tribble et al. |
| 2021/0308385 | A1 | 10/2021 | Nisha et al. |
| 2022/0062964 | A1 | 3/2022 | VanDerWoude et al. |

FOREIGN PATENT DOCUMENTS

| | | | | |
|---|---|---|---|---|
| CA | 2527412 | A1 * | 5/2006 | ........... A61B 5/0002 |
| CA | 2561239 | C | 2/2010 | |
| CA | 2 636 115 | C | 6/2014 | |
| CA | 2 848 274 | C | 9/2016 | |
| CN | 105307548 | A | 2/2016 | |
| CN | 106687960 | A | 5/2017 | |
| CN | 108292523 | A | 7/2018 | |
| CN | 110265108 | A | 9/2019 | |
| CN | 111050688 | A | 4/2020 | |
| EP | 1 973 593 | B1 | 4/2013 | |
| EP | 1 593 076 | B1 | 10/2019 | |
| JP | 2007-304654 | A | 11/2007 | |
| JP | 2016-517077 | A | 6/2016 | |
| JP | 2018-181340 | A | 11/2018 | |
| KR | 10-2014-0129141 | A | 11/2014 | |
| WO | WO-2006/034367 | A2 | 3/2006 | |
| WO | WO-2010/058796 | A1 | 5/2010 | |
| WO | WO-2011014517 | A1 * | 2/2011 | ............. G06F 19/00 |
| WO | WO-2011/035277 | A1 | 3/2011 | |
| WO | WO-2011/039676 | A2 | 4/2011 | |
| WO | WO-2014/055925 | A1 | 4/2014 | |
| WO | WO-2015/187682 | A1 | 12/2015 | |
| WO | WO-2017066741 | A1 * | 4/2017 | ............ A61J 7/0084 |
| WO | WO-2019/028004 | A1 | 2/2019 | |
| WO | WO-2019/031331 | A1 | 2/2019 | |

OTHER PUBLICATIONS

Cakaloglu, T. (Nov. 1, 2017). "Medi-Deep: Deep control in a medication usage." *2017 IEEE International Conference of Bioinfomratice and Biomedicine* (*BIBM*), 899-904. Doi: 10.1109/BIBM.2017.8217776.

Google patents search, May 26, 2020 (Year: 2020) 2 pages.

IP.com Search, Mar. 22, 2021 (Year: 2021), 1 page.

Neuman, M.R. et al. (May 13, 2012), "Advances in Medical Devices and Medical Electronics," in Proceedings of the IEEE, vol. 100, No. Special Centennial Issue, pp. 1537-1550,doi: 10.1109/JPROC.2012.2190684.

Qui et al. (2016) "A survey of machine learning for big data processing." *EURASIP Journal on Advances in Signal Processing*, Article No. 67, 16 pages.

Shishvan, O. Rajabi et al. (2018). "Machine Intelligence in Health-care and Medical Cyber Physical Systems: A Survey." *IEEE Access*. vol. 6, 46419-46494. doi: 10.1109/ACCESS.2018.2866049.

Uniyal, D. et al. (Nov. 7, 2014), "Pervasive Healthcare—A Comprehensive Survey of Tools and Techniques," arXiv:1411.1821v1, 48 pages.

Yang, J., McAuley, J.J., & Leskovec, J. (2013). "Community Detection in Networks with Node Attributes." 2013 IEEE 13th International Conference on Data Mining, 1151-1156.

Yaniv, Z. et al. (Oct. 1, 2016). "The National Library of Medicine Pill Image Recognition Challenge: An Initial Report." *Oct. 2016 IEEE Applied Imagery Pattern Recognition Workshop*, (*AIPR*), 1-9. Doi: 10.1109/AIPR.2016.8010584.

Zhan, A. et al. (Jan. 5, 2016) "High Frequency Remote Monitoring of Parkinson's Disease via Smartphone: Platform Overview and Medication Response Detection," Retrieved Apr. 29, 2021. 12 pages.

Svendsen, K. et al. (2011). "Choosing the Unit of Measurement Counts: The Use of Oral Morphine Equivalents in Studies of Opioid Consumption is a Useful Addition to Defined Daily Doses." Palliative Medicine, vol. 25, No. 7, Oct. 2011, pp. 725-732. DOI.org (Crossref), https://doi.org/10.1177/0269216311398300.

Noonan, F. et al. (2018). "Automation of a paper-based waste tracking system," 2018 2nd International Symposium on Small-scale Intelligent Manufacturing Systems (SIMS), Cavan, Ireland, 2018, pp. 1-5, doi: 10.1109/SI MS.2018.8355290.

* cited by examiner

SYSTEM AND METHOD FOR DISPENSING MEDICATION

CROSS REFERENCE TO RELATED APPLICATION

This application is a continuation of U.S. patent application Ser. No. 15/887,222 filed on Feb. 2, 2018, entitled "SYSTEM AND METHOD FOR DISPENSING MEDICATION". The entire contents of this application is incorporated herein by reference in its entirety.

TECHNICAL FIELD

The subject matter described herein relates generally to the management of pharmaceuticals and more specifically to a system for dispensing medication.

BACKGROUND

Diversion may refer to the transfer of a controlled substance to a third-party who is not legally authorized to receive, possess, and/or consume the controlled substance. High-value and/or controlled prescription medications, notably opiates, opioids, and narcotics, may be especially prone to diversion. For instance, some prescription pain medications, such as morphine, hydromorphone, fentanyl, and/or the like, may be administered to a patient via a patient-controlled analgesia pump. The patient-controlled analgesia pump may be a syringe pump where the syringe may often contain more doses of the pain medication than is needed by the patient. These unused doses of pain medication may be diverted by medical professionals tending to the patient. For example, some of the pain medication may be removed from the syringe before the syringe is loaded into a patient-controlled analgesia pump. Alternatively and/or additionally, any pain medication that remains in the syringe after the syringe is removed from the patient-controlled analgesia pump may be held back instead of properly disposed of at a wasting site.

SUMMARY

Systems, methods, and articles of manufacture, including computer program products, are provided for detecting diversion. In one aspect, there is provided a system. The system may include at least one data processor and at least one memory. The at least one memory may store instructions that result in operations when executed by the at least one data processor. The operations may include: receiving, from a dispensing cabinet including medication, data associated with a plurality of individuals accessing the dispensing cabinet to retrieve and/or return the medication; detecting a diversion of the medication by at least applying, to at least a portion of the data received from the dispensing cabinet, a machine learning model, the machine learning model being trained to detect diversion; determining, based on the data received from the dispensing cabinet, an identity of a first individual responsible for the diversion; and in response to the determination of the first individual as being responsible for the diversion, triggering an investigative workflow at the dispensing cabinet.

In some variations, one or more features disclosed herein including the following features can optionally be included in any feasible combination. The data received from the dispensing cabinet may include one or more videos, images, and/or audio recordings captured at the dispensing cabinet of the plurality of individuals accessing the dispensing cabinet. The machine learning model may be trained to identify, based on the videos, images, and/or audio recordings, one or more physical traits indicative of diversion. The one or more physical traits may include a facial feature, a facial expression, a body posture, a hand gesture, and an eye movement associated with drug abuse and/or theft.

In some variations, the data received from the dispensing cabinet may include a fingerprint, an iris pattern, a retina pattern, a handwritten signature, a voice, an identification number, and/or a passcode of the plurality of individuals accessing the dispensing cabinet.

In some variations, the machine learning model may be trained to detect, based at least in part on the data received from the dispensing cabinet, one or more behavioral patterns associated with diversion. The one or more behavioral patterns may include accessing the dispensing cabinet at inconsistent hours and/or with an abnormal frequency.

In some variations, the investigative workflow may include isolating a first medication returned by the first individual to the dispensing cabinet. The first medication may be isolated in a portion of the dispensing cabinet that is not accessible to a second individual. The portion of dispensing cabinet may be configured to receive the first medication but not a second medication returned by the second individual to the dispensing cabinet.

In some variations, the investigative workflow may include: detecting that the first individual is accessing a drawer in the dispensing cabinet; and in response to the detection of the first individual accessing the drawer in the dispensing cabinet, activating a first camera at the dispensing cabinet to capture a first image and/or a first video of the first individual retrieving the medication from the drawer and/or returning the medication to the drawer. The investigative workflow may further include activating a second camera at the dispensing cabinet to capture a second image and/or a second video of the first individual. The second image and/or the second video may include a face of the first individual to enable a verification of the identity of the first individual.

In some variations, the machine learning model may be trained to perform anomaly detection. The machine learning model may be trained based at least on training data that includes anomalous data indicative of diversion. The machine learning model may be trained to differentiate between the anomalous data and non-anomalous data.

Implementations of the current subject matter can include, but are not limited to, methods consistent with the descriptions provided herein as well as articles that comprise a tangibly embodied machine-readable medium operable to cause one or more machines (e.g., computers, etc.) to result in operations implementing one or more of the described features. Similarly, computer systems are also described that may include one or more processors and one or more memories coupled to the one or more processors. A memory, which can include a non-transitory computer-readable or machine-readable storage medium, may include, encode, store, or the like one or more programs that cause one or more processors to perform one or more of the operations described herein. Computer implemented methods consistent with one or more implementations of the current subject matter can be implemented by one or more data processors residing in a single computing system or multiple computing systems. Such multiple computing systems can be connected and can exchange data and/or commands or other instructions or the like via one or more connections, including, for example, to a connection over a network (e.g. the Internet, a wireless wide area network, a local area network, a wide area network, a wired network, or the like), via a direct connection between one or more of the multiple computing systems, etc.

The details of one or more variations of the subject matter described herein are set forth in the accompanying drawings and the description below. Other features and advantages of the subject matter described herein will be apparent from the description and drawings, and from the claims. While certain features of the currently disclosed subject matter are described for illustrative purposes in relation to web application user interfaces, it should be readily understood that such features are not intended to be limiting. The claims that follow this disclosure are intended to define the scope of the protected subject matter.

DESCRIPTION OF DRAWINGS

The accompanying drawings, which are incorporated in and constitute a part of this specification, show certain aspects of the subject matter disclosed herein and, together with the description, help explain some of the principles associated with the disclosed implementations. In the drawings.

When practical, similar reference numbers denote similar structures, features, or elements.

DETAILED DESCRIPTION

Figure 1:
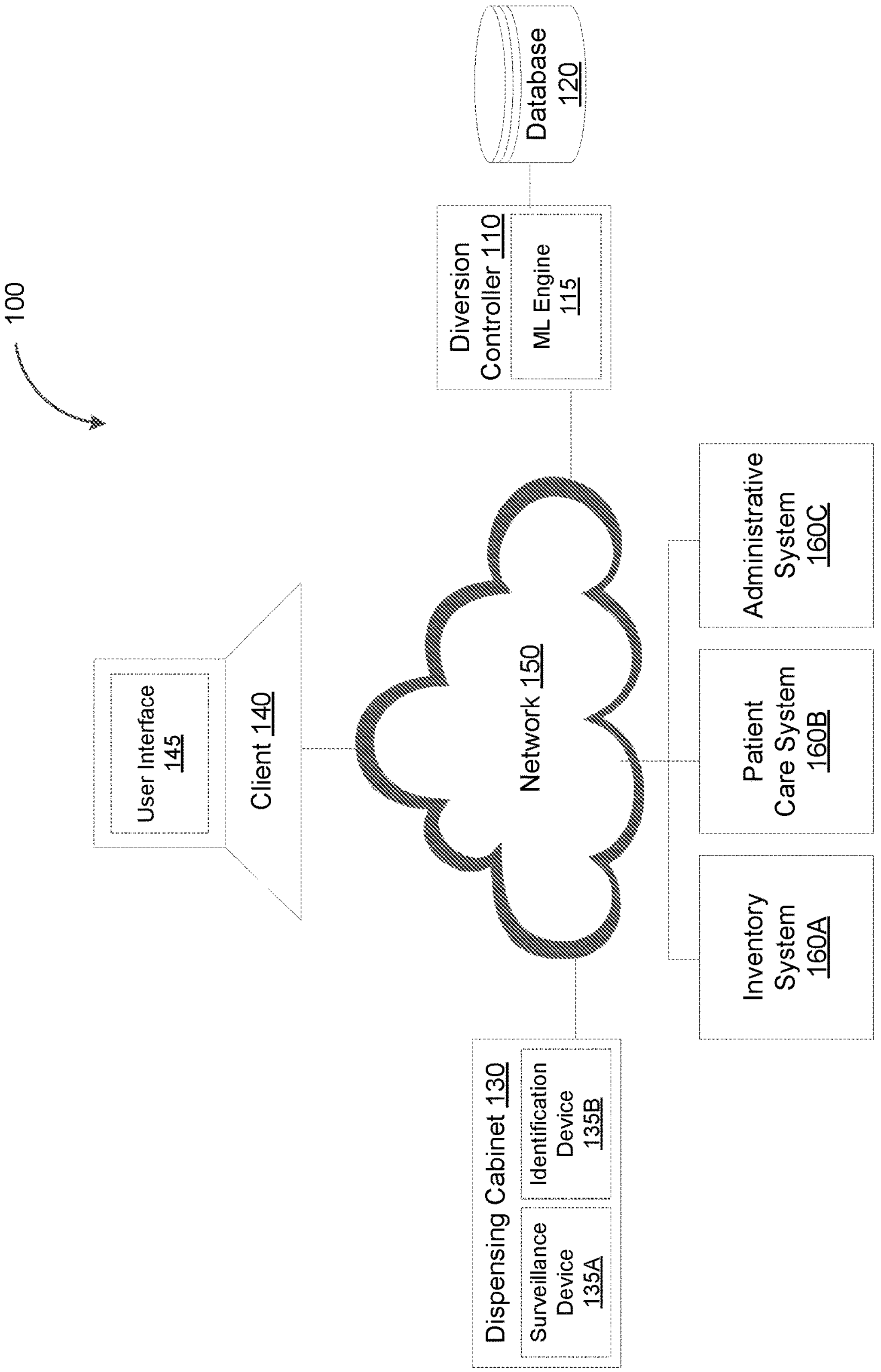
FIG. 1 depicts a system diagram illustrating a medication dispensing system, in accordance with some example embodiments.

Diversion of a medication may occur at any point in time during the compounding, dispensing, administration, and/or wasting of the medication. Prescription pain medications such as, for example, morphine, hydromorphone, fentanyl, and/or the like, may be especially prone to diversion due to a lack sufficient custodial oversight during the dispensing, administration, and wasting of the prescription pain medication. For example, dispensing cabinets at medical facilities may be accessible to multiple medical professionals. Moreover, different medical professionals may be responsible for the dispensing, administration, and wasting of the medication. Thus, even when diversion is detected, it may be difficult to determine when the diversion actually occurred and identify the individuals responsible for the diversion.

In some example embodiments, a dispensing system may be configured to monitor and/or track access to the medication stored in a dispensing cabinet by at least capturing data associated with individuals who access the dispensing cabinet, for example, to retrieve medication and/or return unused medication. For example, the dispensing system may capture images, videos, and/or audio recordings of the individuals accessing the dispensing cabinet. The dispensing system may also perform a biometric scan to capture, for example, a fingerprint, iris pattern, retina pattern, handwritten signature, voice, and/or the like, of the individuals accessing the dispensing cabinet. Alternatively and/or additionally, the dispensing system may be configured to receive an identification number and/or a passcode that uniquely identifies the individuals accessing the dispensing cabinet. By capturing data associated with the individuals accessing the dispensing cabinet, the dispensing system may determine the identity and/or behavioral patterns of the individuals accessing the dispensing cabinet. For example, the dispensing system may determine, based on the data associated with the individuals accessing the dispensing cabinet, the timing and/or frequency with which an individual accesses the dispensing cabinet.

In some example embodiments, the dispensing system may be configured to detect physical traits and/or behavioral patterns associated with diversion. The dispensing system may include machine learning models trained to identify, based the data associated with individuals accessing the dispensing cabinet, physical traits and/or behavioral patterns indicative of diversion. For example, the machine learning models may be trained to identify physical traits indicative of diversion including, for example, facial features, facial expressions, body postures, hand gestures, eye movements, and/or the like, associated with drug abuse. Alternatively and/or additionally, the machine learning models may be trained to identify behavioral patterns indicative of diversion including, for example, accessing the dispensing cabinet at inconsistent times and/or with abnormal frequency, irregularities in wasted and/or returned medications, excessive cancellations and/or overrides, and/or the like. The dispensing system may further identify the individuals who exhibit the physical traits and/or the behavioral patterns associated with diversion. These individuals may be identified as suspects who may be responsible for the diversion.

In some example embodiments, the dispensing system may respond to the identification of individuals who are suspected as being responsible for diversion by at least triggering an investigative workflow at the dispensing cabinet. The investigative workflow may include capturing additional data (e.g., video, images, audio recordings, and/or the like) when individuals suspected of being responsible for diversion access the dispensing cabinet. Alternatively and/or additionally, the investigative workflow may include isolating, at the dispensing cabinet, the unused medication returned to the dispensing cabinet by an individual determined to have one or more physical traits and/or behavioral patterns associated with diversion. For example, the dispensing cabinet may include one or more pockets. A pocket may be any receptacle within the dispensing cabinet including, for example, a drawer in the dispensing cabinet, an enclosure within a drawer of the dispensing cabinet, and/or the like. When an individual is determined to exhibit physical traits and/or behavioral patterns associated with diversion, the dispensing system may isolate the unused medication returned by the individual by at least providing, to that individual, exclusive access to a pocket within the dispensing cabinet. In doing so, the unused medication returned by the individual may be segregated from other medication stored in the dispensing cabinet. A subsequent verification that the individual engaged in diversion may be performed based on the unused medication returned by the individual. For example, the unused medication may be examined for evidence of tampering.

FIG. 1 depicts a system diagram illustrating a medication dispensing system 100, in accordance with some example embodiments. The medication dispensing system 100 may include a diversion controller 110, a dispensing cabinet 130, and a client 140. As shown in FIG. 1, the diversion controller

110, the dispensing cabinet 130, and the client 140 may be communicatively coupled via a network 150. The diversion controller 110 may also be communicatively coupled, via the network 150, with an inventory system 160A, a patient care system 160B, and an administrative system 160C. The network 150 may be any wired and/or wireless network including, for example, a public land mobile network (PLMN), a wide area network (WAN), a local area network (LAN), a virtual local area network (VLAN), the Internet, and/or the like.

In some example embodiments, the dispensing cabinet 130 may be configured to capture data associated with individuals accessing the dispensing cabinet 130, for example, to retrieve medication from the dispensing cabinet 130 and/or return unused medication to the dispensing cabinet 130. Alternatively and/or additionally, the dispensing cabinet 130 may capture data during, for example, logins to and/or logouts from the dispensing cabinet 130, searches for patients and/or medications at the dispensing cabinet 130, patient record reviews, counting and documenting the count of medications in the dispensing cabinet 130, fill and refills of medications, loading and/or unloading medication from the dispensing cabinet 130, documentation of discrepancies, cancellation of transactions (e.g., dispense, fill/refill, load/unload, count, waste, return, and/or the like), and/or the like. Referring again to FIG. 1, the dispensing cabinet 130 may include a surveillance device 135A which may be any recording device including, for example, a video camera, a still image camera, an audio recorder, and/or the like. The surveillance device 135A may be configured to capture images, videos, and/or audio recordings of individuals accessing the dispensing cabinet 130, for example, to retrieve and/or return medication. As shown in FIG. 1, the dispensing cabinet 130 may include an identification device 135B. The identification device 135B may be a biometric reader configured to capture, for example, a fingerprint, iris pattern, retina pattern, handwritten signature, voice, and/or the like, of the individuals accessing the dispensing cabinet 130. Alternatively and/or additionally, the identification device 135B may be configured to receive the identification numbers and/or passcodes of the individuals accessing the dispensing cabinet 130 via, for example, a keyboard and/or a keycard scanner. It should be appreciated that the keycard scanner may obtain this data (e.g., the identification numbers and/or passcodes) in any manner including, for example, near-field communication (NFC), radio frequency identification (RFID), barcodes, quick response (QR) codes, and/or the like.

At least a portion of the data captured at the dispensing cabinet 130, for example, by the surveillance device 135A and/or the identification device 135B, may be sent to the diversion controller 110 via the network 150. Alternatively and/or additionally, the diversion controller 110 may also receive, via the network 150, data from a variety of other sources including, for example, the inventory system 160A, the patient care system 160B, the administrative system 160C, and/or the like. It should be appreciated that the diversion controller 110 may be coupled with any number of computing systems capable of providing data associated with the flow of medication throughout one or more medical facilities including, for example, from being delivered and inducted into the inventory system 160A to being dispensed from the dispensing cabinet 130, administered to patients via the patient care system 160B, and/or ultimately wasted by being disposed of at the dispensing cabinet 130. For example, the inventory system 160A may be configured to track the supply of medication available at one or more medical facilities. The patient care system 160B may include one or more devices for administering medications to patients including, for example, patient controlled analgesic pumps. The administrative system 160C may track the personnel at one or more medical facilities including, for example, personal data, shift schedules, vacation days, and/or the like.

For example, the inventory system 160A, the patient care system 160B, and/or the administrative system 160C may provide electronic medication administration records including, for example, patient records, caregiver records, medication records, and/or the like. The patient records may include, for example, patient identifications, patient locations, demographics, health data (e.g., pain scales, vitals, and/or the like), caregiver assignments, and/or the like. The caregiver records may include, for example, caregiver identifications, caregiver schedules and/or actual times worked, caregiver locations, caregiver patient assignments, and/or the like. The medication records may include, for example, date and/or time of medication administration, identification of administered medications, strength and/or concentration of administered medications, dosage of administered medications, dosage forms of administered medications, date and/or time of medication orders, strength and/or concentration of ordered medications, dosage of ordered medications, dosage form of ordered medications, and/or the like.

The data received at the diversion controller 110 may be evaluated by the diversion controller 110 in real time and/or stored at a database 120 coupled with the diversion controller 110 for evaluation at a later time. In some example embodiments, the diversion controller 110 may include a machine learning engine 115 configured to detect, based on the data received at the diversion controller 110 and/or stored at the database 120, one or more physical traits and/or behavioral patterns associated with diversion. The diversion controller 110 may further identify, as suspects who may be responsible for diversion, one or more of the individuals who access the dispensing cabinet 130 and who exhibit the physical traits and/or behavioral patterns associated with diversion.

Physical traits associated with diversion may include, for example, facial features, expressions, body posture, gestures, eye movements, and/or the like, associated with illicit conduct such as, for example, drug abuse, theft, and/or the like. Meanwhile, behavioral patterns associated with diversion may include accessing the dispensing cabinet at inconsistent times and/or with abnormal frequency, irregularities in wasted and/or returned medications, excessive cancellations and/or overrides, and/or the like. That is, one caregiver assigned to a patient may access the dispensing cabinet at inconsistent times and/or with abnormal frequency relative to other caregivers assigned to the same patient. For example, the caregiver may dispense and document the administration of a higher total dose of medication during their shift than the other caregivers, even when the patient does not report a change in pain. Alternatively and/or additionally, the patient may report inadequate pain relief even though the caregiver administers the same total dose of medication to the patient as the other caregivers assigned to the patient. Abnormally long periods of time may also elapse between when the caregiver dispenses the medication from the dispensing cabinet 130, administers the medication to the patient, and returns the unused medication to the dispensing cabinet 130 for disposal.

In some example embodiments, the machine learning engine 115 may implement one or more machine learning models configured to perform anomaly detection. As used herein, "anomaly detection" may refer to the identification of outliers, which may be one or more items in a dataset that do not conform to an expected pattern associated with the dataset and/or other items in the dataset. Accordingly, the machine learning engine 115 may implement machine learning models capable of differentiating between anomalous data, which may be indicative of diversion, and non-anomalous data. It should be appreciated that non-anomalous data may encompass a range of different behavioral patterns. That is, an individual may exhibit a different behavioral pattern than another individual but a mere difference in behavioral patterns between two individuals does not necessarily indicate diversion. Instead, the machine learning model may be trained to identify anomalous behavior that may not merely be different but fail to conform to an expected pattern.

For example, in some example embodiments, the machine learning engine 115 may apply the one or more machine learning models in order to identify, in the data received at the diversion controller 110 and/or stored at the database 120, anomalous data associated with inconsistent physical traits and/or behavioral patterns which, as noted, may be indicative of diversion. The one or more machine learning models may include any type of machine learning model including, for example, a regression model, an instance-based model, a regularization model, a decision tree, a Bayesian model, a clustering model, an associative model, a neural network, a deep learning model, a dimensionality reduction model, an ensemble model, and/or the like. In some example embodiments, the one or more machine learning models may include an isolation forest although, as noted, different and/or additionally machine learning models may also be used.

In some example embodiments, the machine learning controller 115 may form an isolation forest based on the data received at the diversion controller 110 and/or stored at the database 120. It should be appreciated that the isolation forest may be formed by populating the isolation forest with recursively divided partitions of the data received at the diversion controller 110 and/or stored at the database 120. As noted, the data received at the diversion controller 110 and/or stored at the database 120 may track the flow of medication throughout one or more medical facilities including, for example, from being delivered and inducted into the inventory system 160A to being dispensed from the dispensing cabinet 130, administered to patients via the patient care system 160B, and/or ultimately wasted by being disposed of at the dispensing cabinet 130.

In some example embodiments, forming the isolation forest may include separating anomalous data, which may be indicative of diversion, from non-anomalous data. For example, anomalous data may be isolated toward the root node of the isolation forest whereas non-anomalous data may be isolated toward the leaf nodes of the isolation forest. As such, the machine learning engine 115 may identify the data at the root of node of the isolation forest as anomalous data. This anomalous data may correspond to physical traits and/or behavioral patterns associated with diversion. For example, the anomalous data may include images, videos, and/or audio recordings captured at the dispensing cabinet 130 that depict one or more individuals who exhibit physical traits indicative of diversion including, for example, facial features, facial expressions, body postures, hand gestures, eye movements, and/or the like, associated with drug abuse.

Alternatively and/or additionally, the anomalous data may correspond to behavioral patterns indicative of diversion including, for example, accessing the dispensing cabinet 130 at inconsistent times and/or with abnormal frequency, irregularities in wasted and/or returned medications, excessive cancellations and/or overrides, and/or the like. For example, an individual may be accessing the dispensing cabinet 130 at times that are inconsistent with that individual's scheduled shifts (e.g., as indicated by data from the administrative system 160C). There may also be prolonged periods of delay between when the individual retrieves medication from the dispensing cabinet 130 and when the medication is administered to a patient and/or when unused medication is returned to the dispensing cabinet 130. According to some example embodiments, the diversion controller 110 may identify the individuals associated with this anomalous data as suspects of diversion. In response to the identification of individuals suspected of diversion, the diversion controller 110 may trigger an alert, which may include a notification that may be provided via a user interface 145 at the client 140. For example, the notification may be provided via a short messaging service (SMS) text, an email, a webpage, an application, and/or the like.

According to some example embodiments, the diversion controller 110 may respond to the identification individuals suspected of diversion by at least triggering an investigative workflow at the dispensing cabinet 130. The investigative workflow may include isolating, at the dispensing cabinet 130, the unused medication returned to the dispensing cabinet 130 by an individual determined to have one or more physical traits and/or behavioral patterns associated with diversion. It should be appreciated that the investigative workflow may also be triggered randomly, for example, to isolate unused medication returned by individuals who have not been identified as being suspected of diversion. Triggering the investigative workflow randomly to include at least some individuals who are not suspected of diversion may prevent alerting the individuals who are suspected of diversion to an ongoing investigation. Furthermore, as part of the investigative workflow, unused medication may be returned to an isolated area of the dispensing cabinet 130 instead of being discarded, for example, as part of a conventional wasting procedure.

To isolate the unused medication returned by the individual, the diversion controller 110 may provide, to the individual, exclusive access to a pocket within the dispensing cabinet 130 that is separate from other areas of the dispensing cabinet 130, which may be accessible to other individuals. The individual may place the unused medication within that pocket, thereby separating the unused medication returned by the individual from other medication stored in the dispensing cabinet 130. The unused medication may be subsequently retrieved from the pocket and examined for evidence of actual diversion including, for example, irregularities in the quantity (e.g., volume) of unused medication, the quality (e.g., concentration) of unused medication, and/or the like. For example, the diversion controller 110 may trigger the investigative workflow and isolate unused medication returned to the dispensing cabinet 130 when the diversion controller 110 determines that an abnormal length of time has elapsed since when medication is administered to a patient and when unused portions of the medication is returned to the dispensing cabinet. The unused medication returned of the dispensing cabinet 130 may be subsequently be subject to various testing, for example, to verify both the quantity (e.g., volume) and quantity (e.g., concentration) of the used medication returned to the dispensing cabinet by an individual suspected of diversion. However, as noted, the diversion controller 110 may also randomly isolate some of the unused medication returned to the dispensing cabinet 130 including, for example, unused medication returned by individuals who have not been identified as suspects of diversion.

Alternatively and/or additionally, the investigative workflow may include triggering the collection of additional data at the dispensing cabinet 130. For example, when an individual is identified as a suspect for diversion, the surveillance device 135A at the dispensing cabinet 130 may be configured to capture additional images, videos, and/or audio recordings of that individual when, for example, the identification device 135B determines that the individual is accessing the dispensing cabinet. The surveillance device 135A may, for instance, move one or more cameras, change the focus and/or zoom of one or more cameras, and/or activate additional cameras in order to capture images and/or videos of the individual at specific angles such as, for example, overhead shots of the individual's hands manipulating medication within the dispensing cabinet 130.

Figure 2:
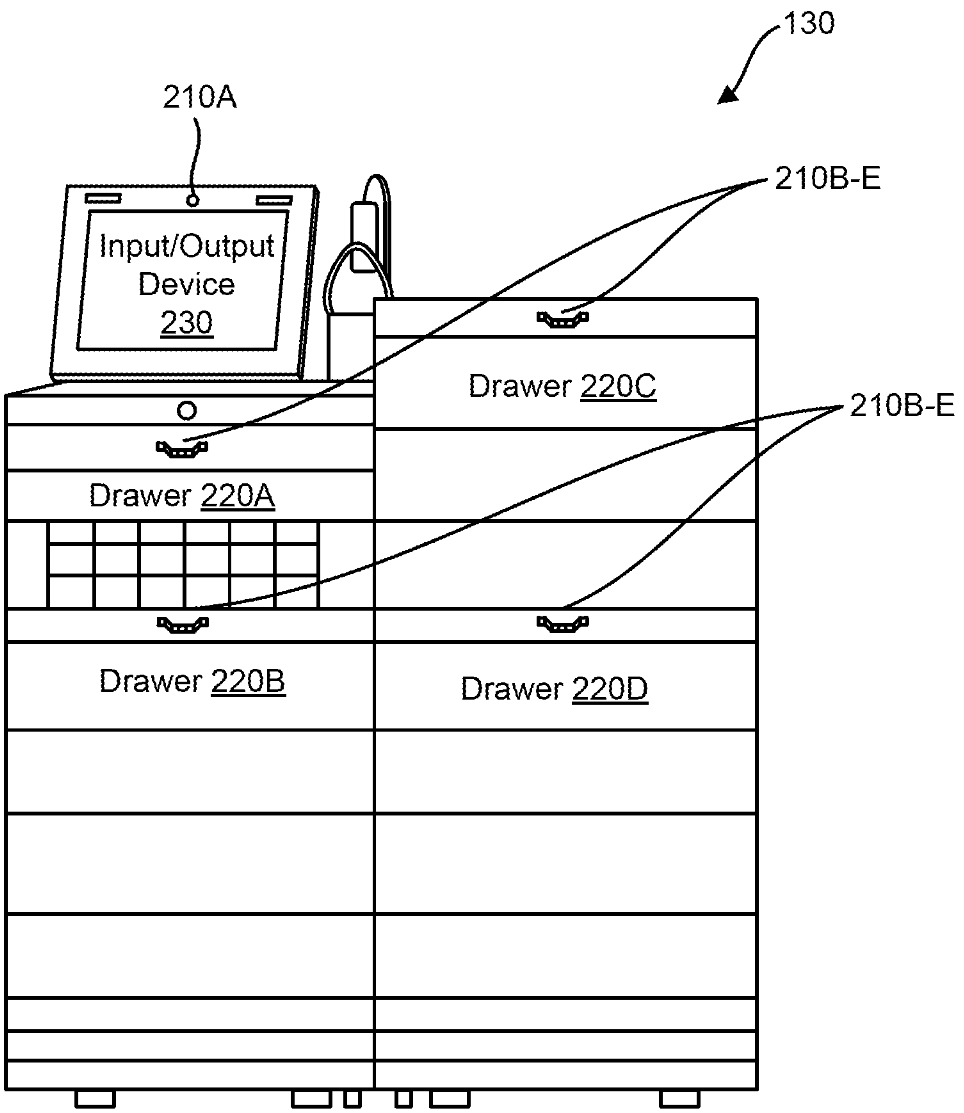
FIG. 2 depicts a dispensing cabinet, in accordance with some example embodiments.

To further illustrate, FIG. 2 depicts the dispensing cabinet 130, in accordance with some example embodiments. Referring to FIG. 2, the dispensing cabinet 130 may include a plurality of drawers including, for example, a first drawer 220A, a second drawer 220B, a third drawer 220C, a fourth drawer 220D, and/or the like. The surveillance device 135A of the dispensing cabinet may include a plurality of cameras including, for example, a first camera 210A, a second camera 210B, a third camera 210C, a fourth camera 210D, a fifth camera 210E, and/or the like. Meanwhile, the dispensing cabinet 130 may further include an input/output device 230, which may include a keyboard, a monitor, a touchscreen, and/or the like. It should be appreciated that the input/output device 230 may be part of the identification device 135B. For example, an individual accessing the dispensing cabinet 130 may enter, via the input/output device 230, an identification number and/or a passcode that uniquely identifies the individual. Moreover, the dispensing cabinet 130 may include a different quantity of cameras and/or drawers than shown.

As shown in FIG. 2, each camera in the surveillance device 135A may have a different field of view. For example, the first camera 210A may be a front facing camera configured to capture images and/or videos that include the face of the individuals who access the dispensing cabinet 130. The first camera 210A may be activated when an individual interacts with the input/output device 230. Meanwhile, the second camera 210B, the third camera 210C, the fourth camera 210D, and the fifth camera 210E may be downward facing cameras configured to capture images and/or videos of the interiors of the corresponding drawers. For example, the second camera 210B may be activated in response to the first drawer 220A being opened. The second camera 210B may further capture images and/or videos of medication being removed from and/or returned to the first drawer 220A. Alternatively and/or additionally, the third camera 210C may be activated in response to the second drawer 220B being opened. The third camera 210C may capture images and/or videos of medication being removed from and/or returned to the second drawer 220B.

In some example embodiments, the first camera 210A, the second camera 210B, the third camera 210C, the fourth camera 210D, and/or the fifth camera 210E may be activated whenever an individual accesses the dispensing cabinet 130. Alternatively and/or additionally, the first camera 210A, the second camera 210B, the third camera 210C, the fourth camera 210D, and/or the fifth camera 210E may be activated as part of an investigative workflow that is triggered whenever an individual suspected of diversion accesses the dispensing cabinet 130. For example, when an individual suspected of diversion accesses the dispensing cabinet 130 and returns unused medication to the first drawer 220A, the second camera 220B may be activated in order to capture images and/or videos of the individual returning the unused medication to the first drawer 220A. These images and/or videos may provide evidence of diversion including, for example, efforts to tamper with the unused medication. Alternatively and/or additionally, the first camera 220A may also be activated in order to capture images and/or videos that includes the face of the individual. These images and/or videos may be used to corroborate the identity of the individual returning the medication to the dispensing cabinet 130.

Figure 3:
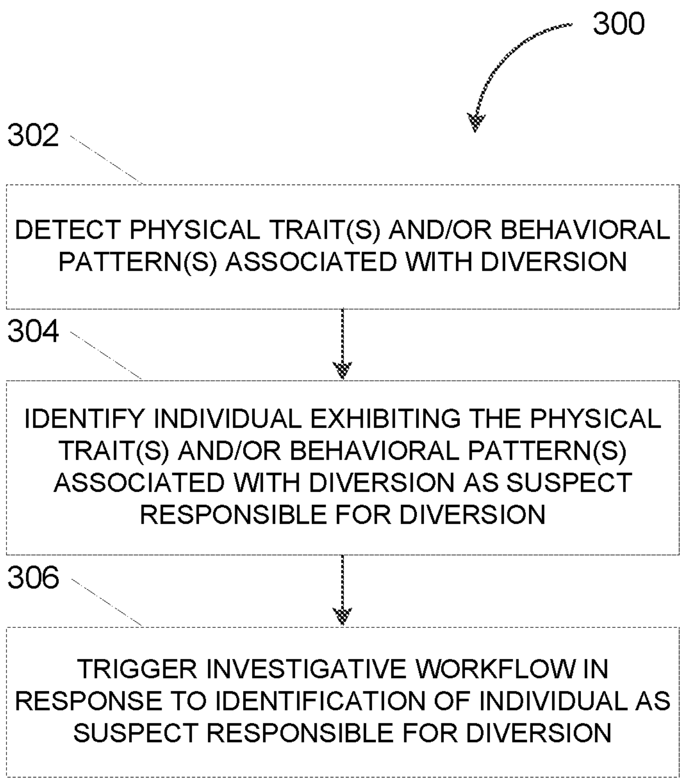
FIG. 3 depicts a flowchart illustrating a process for dispensing medication, in accordance with some example embodiments.

FIG. 3 depicts a flowchart illustrating a process 300 for dispensing medication, in accordance with some example embodiments. Referring to FIGS. 1-3, the process 300 may be performed by the diversion controller 110.

At 302, the diversion controller 110 may detect one or more physical traits and/or behavioral patterns associated with diversion of a medication. In some example embodiments, the diversion controller 110 may detect physical traits associated with diversion including, for example, facial features, facial expressions, body postures, hand gestures, eye movements, and/or the like, associated with drug abuse. Alternatively and/or additionally, the anomalous data may correspond to behavioral patterns indicative of diversion including, for example, accessing a dispensing cabinet (e.g., the dispensing cabinet 130) at inconsistent times and/or with abnormal frequency, irregularities in wasted and/or returned medications, excessive cancellations and/or overrides, and/or the like. As noted, the diversion controller 110 may include the machine learning engine 115, which may implement one or more machine learning models configured to perform anomaly detection in order to identify physical traits and/or behavioral patterns associated with diversion. For example, the one or more machine learning models may be any type of machine learning model including, for example, an isolation forest, a regression model, an instance-based model, a regularization model, a decision tree, a Bayesian model, a clustering model, an associative model, a neural network, a deep learning model, a dimensionality reduction model, an ensemble model, and/or the like.

At 304, the diversion controller 110 may identify an individual exhibiting the one or more physical traits and/or behavioral patterns associated with diversion as a suspect responsible for the diversion. For example, the dispensing cabinet 130 may include the identification device 135B, which may capture and/or receive data (e.g., a fingerprint, an iris pattern, a retina pattern, a handwritten signature, a voice, an identification number, a passcode) that enables the identification of individuals who accesses the dispensing cabinet 130. Identifying the individuals who accesses the dispensing cabinet 130 may further enable the data captured at the dispensing cabinet 130 to be associated with specific individuals. As such, the diversion controller 110 may be able to determine the identities of the individuals who exhibit the physical traits and/or behavioral patterns associated with diversion. In doing so, the diversion controller 110 may trigger an investigative workflow for those specific individuals.

At 306, the diversion controller 110 may trigger an investigative workflow at the dispensing cabinet 130 in response to the identification of the individual as the suspect responsible for the diversion. In some example embodiments, the investigative workflow may include isolating, at the dispensing cabinet 130, the unused medication returned to the dispensing cabinet 130 by the individual exhibiting the physical traits and/or behavioral patterns associated with diversion. The unused medication may be isolated by providing the individual with exclusive access to a pocket within the dispensing cabinet 130 that is separate from other areas of the dispensing cabinet 130, which may be accessible to other individuals. Alternatively and/or additionally, the investigative workflow may include triggering the collection of additional data at the dispensing cabinet 130. For example, when the individual accesses the dispensing cabinet 130 to return unused medication to the first drawer 220A, the second camera 210B may be activated in order to capture images and/or videos of medication being removed from the first drawer 220A of the dispensing cabinet while the first camera 210A may be activated in order to capture images and/or videos that includes a face of the individual.

Figure 4:
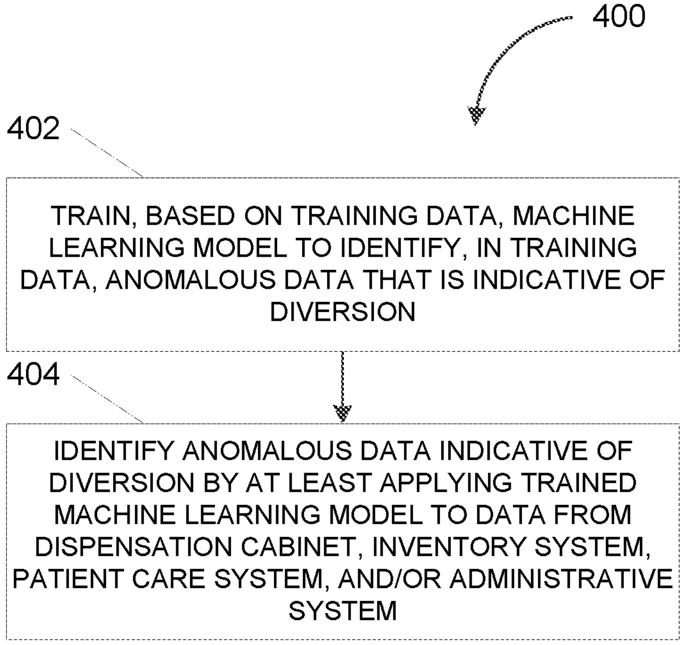
FIG. 4 depicts a flowchart illustrating a process for detecting diversion, in accordance with some example embodiments.

FIG. 4 depicts a flowchart illustrating a process 400 for detecting diversion of an opioid pain medication, in accordance with some example embodiments. Referring to FIG. 4, the process 400 may be performed by the diversion controller 110 and may implement operation 302 of the process 300.

At 402, the diversion controller 110 may train, based on training data, a machine learning model to identify, in the training data, anomalous data that is indicative of diversion. In some example embodiments, the one or more machine learning models may be any type of machine learning model including, for example, an isolation forest, a regression model, an instance-based model, a regularization model, a decision tree, a Bayesian model, a clustering model, an associative model, a neural network, a deep learning model, a dimensionality reduction model, an ensemble model, and/or the like.

In some example embodiments, the one or more machine learning models may be an isolation forest, in which case the training of the machine learning model may include building an isolation forest based on the training data. Here, the isolation forest may be subject to unsupervised training, which may be based on unlabeled training data. That is, the isolation forest may be trained based on training data that has not been labeled to differentiate between anomalous data (e.g., indicative of diversion) and non-anomalous data. Instead, training the machine learning model may include building the isolation forest by at least populating the isolation forest with recursively divided partitions of the training data until the anomalous data included in the training data is isolated towards the root node of the isolation forest and the non-anomalous data included in the training data is isolated towards the leaf nodes of the isolation forest.

Alternatively and/or additionally, the machine learning model may be subject to supervised training, which may use labeled training data instead of the unlabeled training data used for unsupervised training. During supervised training, the diversion controller 110 may train the machine learning model using training data that is known to be associated with anomalous behavior and is labeled as such. The diversion controller 110 may also train the machine learning model using training data that is known to be associated with non-anomalous behavior and/or is labeled as non-anomalous. In some example embodiments, the supervised training of the machine learning model may include adjusting the machine learning model including, for example, the weights and/or biases applied by the machine learning model, to minimize an error in the output of the machine learning model. For instance, during supervised training, the machine learning model may be adjusted, for example, by at least back propagating any errors present in the output of the machine learning model and performing gradient descent, until the machine learning model outputs the correct classifications for the training data. It should be appreciated that the correct classifications for the training data may match the labels associated with the training data.

At 404, the diversion controller 110 may identify anomalous data indicative of diversion by at least applying the trained machine learning model to data from the dispensing cabinet 130, the inventory system 160A, the patient care system 160B, and/or the administrative system 160C. As noted, in some example embodiments, the diversion controller 110 may apply an isolation forest in order to identify anomalous data indicative of diversion. Accordingly, to identify anomalous data, the diversion controller 110 may add, to the isolation forest formed in operation 404, data received at the diversion controller 110 and/or stored at the database 120, which may include data tracking the flow of medication throughout one or more medical facilities.

Anomalous data in the data received at the diversion controller 110 and/or stored at the database 120 may be isolated towards the root node of the isolation forest whereas non-anomalous data may be isolated towards the leaf nodes of the isolation forest. As such, the diversion controller 110 may identify the data at the root of node of the isolation forest as anomalous data. This anomalous data may correspond to physical traits and/or behavioral patterns associated with diversion. For example, the anomalous data may include images, videos, and/or audio recordings captured at the dispensing cabinet 130 that depict one or more individuals who exhibit physical traits indicative of diversion including, for example, facial features, facial expressions, body postures, hand gestures, eye movements, and/or the like, associated with drug abuse. Alternatively and/or additionally, the anomalous data may correspond to behavioral patterns indicative of diversion including, for example, accessing the dispensing cabinet 130 at inconsistent times and/or with abnormal frequency, irregularities in wasted and/or returned medications, excessive cancellations and/or overrides, and/or the like.

Figure 5:
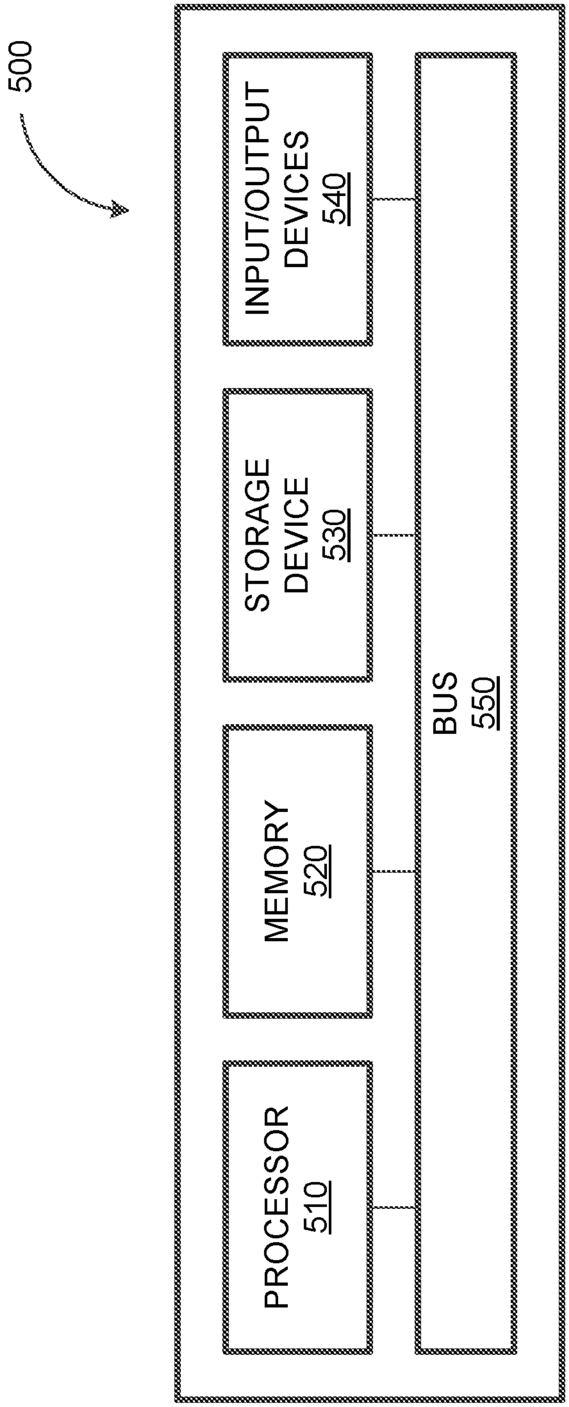
FIG. 5 depicts a block diagram illustrating a computing system, in accordance with some example embodiments.

FIG. 5 depicts a block diagram illustrating a computing system 500 consistent with implementations of the current subject matter. Referring to FIGS. 1 and 5, the computing system 500 can be used to implement the diversion controller 110 and/or any components therein.

As shown in FIG. 5, the computing system 500 can include a processor 510, a memory 520, a storage device 530, and input/output devices 540. The processor 510, the memory 520, the storage device 530, and the input/output devices 540 can be interconnected via a system bus 550. The processor 510 is capable of processing instructions for execution within the computing system 500. Such executed instructions can implement one or more components of, for example, the diversion controller 110. In some example embodiments, the processor 510 can be a single-threaded processor. Alternatively, the processor 510 can be a multi-threaded processor. The processor 510 is capable of processing instructions stored in the memory 520 and/or on the storage device 530 to display graphical information for a user interface provided via the input/output device 540.

The memory 520 is a computer readable medium such as volatile or non-volatile that stores information within the computing system 500. The memory 520 can store data structures representing configuration object databases, for example. The storage device 530 is capable of providing persistent storage for the computing system 500. The storage device 530 can be a floppy disk device, a hard disk device, an optical disk device, or a tape device, or other suitable persistent storage means. The input/output device 540 provides input/output operations for the computing system 500. In some example embodiments, the input/output device 540 includes a keyboard and/or pointing device. In various implementations, the input/output device 540 includes a display unit for displaying graphical user interfaces.

According to some example embodiments, the input/output device 540 can provide input/output operations for a network device. For example, the input/output device 540 can include Ethernet ports or other networking ports to communicate with one or more wired and/or wireless networks (e.g., a local area network (LAN), a wide area network (WAN), the Internet).

In some example embodiments, the computing system 500 can be used to execute various interactive computer software applications that can be used for organization, analysis and/or storage of data in various formats. Alternatively, the computing system 500 can be used to execute any type of software applications. These applications can be used to perform various functionalities, e.g., planning functionalities (e.g., generating, managing, editing of spreadsheet documents, word processing documents, and/or any other objects, etc.), computing functionalities, communications functionalities, etc. The applications can include various add-in functionalities or can be standalone computing products and/or functionalities. Upon activation within the applications, the functionalities can be used to generate the user interface provided via the input/output device 540. The user interface can be generated and presented to a user by the computing system 500 (e.g., on a computer screen monitor, etc.).

One or more aspects or features of the subject matter described herein can be realized in digital electronic circuitry, integrated circuitry, specially designed ASICs, field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which can also be referred to as programs, software, software applications, applications, components, or code, include machine instructions for a programmable processor, and can be implemented in a high-level procedural and/or object-oriented programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example, as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including acoustic, speech, or tactile input. Other possible input devices include touch screens or other touch-sensitive devices such as single or multi-point resistive or capacitive track pads, voice recognition hardware and software, optical scanners, optical pointers, digital image capture devices and associated interpretation software, and the like.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flows depicted in the accompanying figures and/or described herein do not necessarily require the particular order shown, or sequential order, to achieve desirable results. Other implementations may be within the scope of the following claims.

What is claimed is:

1. A system, comprising:

a dispensing cabinet having a plurality of drawers including a predetermined drawer;

at least one data processor; and at least one memory storing instructions which, when executed by the at least one data processor, result in operations comprising:

receiving, from the dispensing cabinet including medication, data associated with a plurality of individuals accessing the dispensing cabinet to retrieve and/or return the medication, the data including one or more videos, images and/or audio recordings;

detecting a diversion of the medication by at least applying, to at least a portion of the data received from the dispensing cabinet, a machine learning model, the machine learning model being trained to identify, based on the data, one or more physical traits indicative of diversion;

determining, based on the data received from the dispensing cabinet, an identity of a first individual responsible for the diversion;

in response to the determination of the first individual as being responsible for the diversion, causing a signal to be sent to the cabinet to provide access to a designated portion of the dispensing cabinet configured to receive a first medication returned by the first individual to the dispensing cabinet, a second individual accessing the dispensing cabinet to return a second medication being provided access to a different portion of the dispensing cabinet such that the first medication returned by the first individual is isolated from one or more medications returned by other individuals to the dispensing cabinet;

causing a signal to be sent to the cabinet to physically isolate the first medication returned by the first individual in the predetermined drawer of the dispensing cabinet; and triggering, based on the application of the one or more physical traits identified by the machine learning model, an investigative workflow that includes retrieving the first medication from the designated portion of the dispensing cabinet and causing the first medication to be examined for evidence of actual diversion including irregularities in quantity or quality of the first medication.

2. The system of claim 1, wherein the data received from the dispensing cabinet includes one or more videos, images, and/or audio recordings captured at the dispensing cabinet of the plurality of individuals accessing the dispensing cabinet.

3. The system of claim 2, wherein the machine learning model is trained to identify, based on the videos, images, and/or audio recordings, one or more physical traits indicative of diversion, and wherein the one or more physical traits include a facial feature, a facial expression, a body posture, a hand gesture, and an eye movement associated with drug abuse and/or theft.

4. The system of claim 1, wherein the data received from the dispensing cabinet includes a fingerprint, an iris pattern, a retina pattern, a handwritten signature, a voice, an identification number, and/or a passcode of the plurality of individuals accessing the dispensing cabinet.

5. The system of claim 1, wherein the machine learning model is trained to detect, based at least in part on the data received from the dispensing cabinet, one or more behavioral patterns associated with diversion, and wherein the one or more behavioral patterns include accessing the dispensing cabinet at inconsistent hours and/or with an abnormal frequency.

6. The system of claim 1, wherein the designated portion of dispensing cabinet is inaccessible to the second individual such that the designated portion of the dispensing cabinet receives the first medication but not the second medication returned by the second individual.

7. The system of claim 1, further comprising:

detecting that the first individual is accessing a drawer in the dispensing cabinet; and in response to the detection of the first individual accessing the drawer in the dispensing cabinet, activating a first camera at the dispensing cabinet to capture a first image and/or a first video of the first individual retrieving the medication from the drawer and/or returning the medication to the drawer.

8. The system of claim 7, further comprising:

activating a second camera at the dispensing cabinet to capture a second image and/or a second video of the first individual, and wherein the second image and/or the second video includes a face of the first individual to enable a verification of the identity of the first individual.

9. The system of claim 1, wherein the machine learning model is trained based on training data that has not been labeled to differentiate between anomalous data indicative of diversion and non-anomalous data.

10. A computer-implemented method, comprising:

receiving, from a dispensing cabinet including medication, data associated with a plurality of individuals accessing the dispensing cabinet to retrieve and/or return the medication, the data including one or more videos, images and/or audio recordings;

detecting a diversion of the medication by at least applying, to at least a portion of the data received from the dispensing cabinet, a machine learning model, the machine learning model being trained to identify, based on the data, one or more physical traits indicative of diversion;

determining, based on the data received from the dispensing cabinet, an identity of a first individual responsible for the diversion;

in response to the determination of the first individual as being responsible for the diversion, causing a signal to be sent to the cabinet to provide access to a designated portion of the dispensing cabinet configured to receive a first medication returned by the first individual to the dispensing cabinet, a second individual accessing the dispensing cabinet to return a second medication being provided access to a different portion of the dispensing cabinet such that the first medication returned by the first individual is isolated from one or more medications returned by other individuals to the dispensing cabinet;

causing a signal to be sent to the cabinet to physically isolate the first medication returned by the first individual in a predetermined drawer of the dispensing cabinet; and triggering, based on the application of the one or more physical traits identified by the machine learning model, an investigative workflow that includes retrieving the first medication from the designated portion of the dispensing cabinet and causing the first medication to be examined for evidence of actual diversion including irregularities in quantity or quality of the first medication.

11. The method of claim 10, wherein the data received from the dispensing cabinet includes one or more videos, images, and/or audio recordings captured at the dispensing cabinet of the plurality of individuals accessing the dispensing cabinet.

12. The method of claim 11, wherein the machine learning model is trained to identify, based on the videos, images, and/or audio recordings, one or more physical traits indicative of diversion, and wherein the one or more physical traits include a facial feature, a facial expression, a body posture, a hand gesture, and an eye movement associated with drug abuse and/or theft.

13. The method of claim 10, wherein the data received from the dispensing cabinet includes a fingerprint, an iris pattern, a retina pattern, a handwritten signature, a voice, an identification number, and/or a passcode of the plurality of individuals accessing the dispensing cabinet.

14. The method of claim 10, wherein the machine learning model is trained to detect, based at least in part on the data received from the dispensing cabinet, one or more behavioral patterns associated with diversion, and wherein the one or more behavioral patterns include accessing the dispensing cabinet at inconsistent hours and/or with an abnormal frequency.

15. The method of claim 10, wherein the designated portion of dispensing cabinet is inaccessible to the second individual such that the designated portion of the dispensing cabinet receives the first medication but not the second medication returned by the second individual.

16. The method of claim 10, further comprising:

detecting that the first individual is accessing a drawer in the dispensing cabinet; and in response to the detection of the first individual accessing the drawer in the dispensing cabinet, activating a first camera at the dispensing cabinet to capture a first image and/or a first video of the first individual retrieving the medication from the drawer and/or returning the medication to the drawer.

17. The method of claim 16, further comprising:

activating a second camera at the dispensing cabinet to capture a second image and/or a second video of the first individual, and wherein the second image and/or the second video includes a face of the first individual to enable a verification of the identity of the first individual.

18. The method of claim 10, wherein the machine learning model is trained based on training data that has not been labeled to differentiate between anomalous data indicative of diversion and non-anomalous data.

19. A non-transitory computer readable medium including instructions, which when executed by at least one data processor, result in operations comprising:

receiving, from a dispensing cabinet including medication, data associated with a plurality of individuals accessing the dispensing cabinet to retrieve and/or return the medication, the data including one or more videos, images and/or audio recordings;

detecting a diversion of the medication by at least applying, to at least a portion of the data received from the dispensing cabinet, a machine learning model, the machine learning model being trained to identify, based on the data, one or more physical traits indicative of diversion;

determining, based on the data received from the dispensing cabinet, an identity of a first individual responsible for the diversion;

in response to the determination of the first individual as being responsible for the diversion, causing a signal to be sent to the cabinet to provide access to a designated portion of the dispensing cabinet configured to receive a first medication returned by the first individual to the dispensing cabinet, a second individual accessing the dispensing cabinet to return a second medication being provided access to a different portion of the dispensing cabinet such that the first medication returned by the first individual is isolated from one or more medications returned by other individuals to the dispensing cabinet;

causing a signal to be sent to the cabinet to physically isolate the first medication returned by the first individual in a predetermined drawer of the dispensing cabinet; and triggering, based on the application of the one or more physical traits identified by the machine learning model, an investigative workflow that includes retrieving the first medication from the designated portion of the dispensing cabinet and causing the first medication to be examined for evidence of actual diversion including irregularities in quantity or quality of the first medication.

20. An apparatus, comprising:

means for receiving, from a dispensing cabinet including medication, data associated with a plurality of individuals accessing the dispensing cabinet to retrieve and/or return the medication, the data including one or more videos, images and/or audio recordings;

means for detecting a diversion of the medication by at least applying, to at least a portion of the data received from the dispensing cabinet, a machine learning model, the machine learning model being trained to identify, based on the data, one or more physical traits indicative of diversion;

means for determining, based on the data received from the dispensing cabinet, an identity of a first individual responsible for the diversion;

means for responding to the first individual being determined as responsible for the diversion by causing a signal to be sent to the cabinet to provide access to a designated portion of the dispensing cabinet configured to receive a first medication returned by the first individual to the dispensing cabinet, a second individual accessing the dispensing cabinet to return a second medication being provided access to a different portion of the dispensing cabinet such that the first medication returned by the first individual is isolated from one or more medications returned by other individuals to the dispensing cabinet;

means for causing a signal to be sent to the cabinet to physically isolate the first medication returned by the first individual in a predetermined drawer of the dispensing cabinet;

means for triggering, based on the application of the one or more physical traits identified by the machine learning model, an investigative workflow that includes retrieving the first medication from the designated portion of the dispensing cabinet and causing the first medication to be examined for evidence of actual diversion including irregularities in quantity or quality of the first medication.

* * * * *